US00PP07931P

United States Patent [19]

van der Knaap

[11] Patent Number: Plant 7,931

[45] Date of Patent: Aug. 4, 1992

[54] CHRYSANTHEMUM PLANT — CORAL MONEYMAKER CULTIVAR

[75] Inventor: Jacques C. M. van der Knaap, De Lier, Netherlands

[73] Assignee: Fides Beheer B.V., De Lier, Netherlands

[21] Appl. No.: 578,473

[22] Filed: Sep. 5, 1990

[51] Int. Cl.[5] ..... A01H 5/00

[52] U.S. Cl. ..... Plt./79

[58] Field of Search ..... Plt./74, 82.2, 82.3, Plt./82.4

[56] References Cited

U.S. PATENT DOCUMENTS

P.P. 6,341 10/1988 Van der Knaap ..... Plt. 74

P.P. 6,851 6/1989 Van Wingerden ..... Plt. 74

P.P. 6,868 6/1989 Van der Knaap ..... Plt. 74

*Primary Examiner*—Howard J. Locker

*Attorney, Agent, or Firm*—Burns, Doane, Swecker & Mathis

[57] ABSTRACT

A new and distinct cultivar of Chrysanthemum plant named Coral Moneymaker is provided. The new cultivar was the result of a naturally occurring mutation of unknown causation and was discovered among plants of the Moneymaker cultivar (U.S. Plant Pat. No. 6,341). The blossoms of the new cultivar exhibit an attractive coral somewhat salmon-orange coloration which can be readily distinguished from the light pink to pinkish-white blossom coloration of the parent cultivar. The new cultivar is particularly suited for use as in the production of a cut anemone spray.

1 Drawing Sheet

SUMMARY OF THE INVENTION

The present invention comprises a new and distinct cultivar of *Dendranthema morifolium* Ramat., and hereinafter is referred to by the cultivar name Coral Moneymaker.

The new cultivar is a mutation of unknown causation which was discovered and carefully preserved during October, 1987 during the course of plant selection work which was conducted by me. The new cultivar was discovered among plants of Moneymaker cultivar (U.S. Plant Pat. No. 6,341) being grown under my direct supervision at De Lier, The Netherlands, which formed blossoms having the characteristic light pink to pinkish-white coloration.

It was observed that a single plant consistently formed blossoms having a distinctive coral coloration. Had I not discovered, carefully studied, and preserved this new cultivar it would have been lost to mankind. This new cultivar is particularly well suited for growing in the production of an attractive cut anemone spray.

Asexual reproduction of the new cultivar by cuttings, as performed at De Lier, The Netherlands, has demonstrated that the characteristics of the new cultivar as herein disclosed are firmly fixed and are retained through successive generations of asexual propagation.

Coral Moneymaker has not been observed under all possible environmental conditions to date. Accordingly, it is possible that the phenotype may vary somewhat with variations in the environment, such as temperature, light, day length, contact with pesticides and/or subjection to growth retardant treatments. The overall combination of characteristics is capable of well distinguishing the new Coral Moneymaker cultivar from all other known Chrysanthemum cultivars.

BRIEF DESCRIPTION OF THE PHOTOGRAPH

The accompanying photograph shows as nearly true as it is reasonably possible to make the same in a color illustration of this character, a typical specimen of the overall plant of the new cultivar wherein the distinctive blossom coloration is apparent. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 to 12:00 a.m. under natural daylight conditions on May 2, 1990 at De Lier, The Netherlands.

Classification:

*Botanical.*—*Dendranthema morifolium* Ramat., cv. Coral Moneymaker.

*Commercial.*—Cut anemone spray.

INFLORESCENCE

A. Capitulum:

*Form.*—Flat.

*Type.*—Anemone.

*Diameter across face.*—Approximately 55 mm. on average.

*Diameter across disc.*—Approximately 32 mm. on average.

B. Corolla of ray and disc florets:

*Color (general tonality from a distance of one meter)*—Coral and somewhat salmon-orange.

*Color (rays).*—Red Group 37D.

*Color (disc).*—Green to coral pink, Greyed-Green Group 193A to Red Group 37A.

*Number of ray florets.*—Approximately 24 on average.

*Number of disc florets.*—Approximately 130 to 140 on average.

The blossom coloration may vary somewhat depending upon the growing season, and the growing conditions.

C. Reproductive organs:

*Androecium.*—Present only in disc florets; numerous.

*Gynoecium.*—Present in both ray and disc florets; numerous.

*Fragrance.*—Normal.

PLANT

A. General appearance:

*Height.*—Approximately 90 cm. on average.

B. Foliage:

*Color (upper surface).*—Green Group 137A.

*Color (under surface).*—Green Group 137B.

*Shape.*—Deeply serrated.

*Leaf size.*—Approximately 150×90 mm. on average.

*Branching laterals.*—Approximately 16 in number on average.

The plants of the new Coral Moneymaker cultivar readily can be distinguished from the parent Moneymaker cultivar (U.S. Plant Pat. No. 6,341) as well as its sister cultivars, California Moneymaker (U.S. Plant Pat. No. 6,851) and Pink Moneymaker (U.S. Plant Pat. No. 6,868), both with respect to blossom coloration and other characteristics. The following data was obtained during November 1991 by a comparison of plants of the Moneymaker, Pink Moneymaker and Coral Moneymaker cultivars growing in a nursery at De Lier, The Netherlands.

| | MONEY-MAKER Cultivar | PINK MONEY-MAKER Cultivar | CORAL MONEY-MAKER Cultivar |
|---|---|---|---|
| Ray Floret Coloration | Red Group 36D | Red Group 36B to Red-Purple Group 65D | Red Group 37D |
| Disc Floret Coloration | Orange Group 27B to Red Group 36D | Yellow-Green Group 145B to Red Group 36B | Greyed-Green Group 193A to Red Group 37A |
| Number of Ray Florets (on average) | 27 | 33 | 24 |
| Number of Disc Florets (on average) | 150–160 | 140–150 | 130–140 |
| Fragrance | normal | normal | normal |
| Flower Diameter | 50 mm. | 45 mm. | 55 mm. |
| Disc Diameter | 28 mm. | not determined | 32 mm. |
| Number of Laterals (average) | 13 | 17 | 16 |
| Typical Leaf Size | 110 × 80 mm. | 100 × 95 mm. | 105 × 90 mm. |
| Foliage Coloration | Green Group 137A | Green Group 137A | Yellow-Green Group 147A |

The California Moneymaker cultivar can be similarly distinguished in view of its rose-purple blossom coloration as illustrated in U.S. Plant Pat. No. 6,851.

I claim:

1. A new and distinct cultivar of Chrysanthemum plant named Coral Moneymaker, substantially as herein shown and described, which exhibits coral somewhat salmon-orange blossoms.

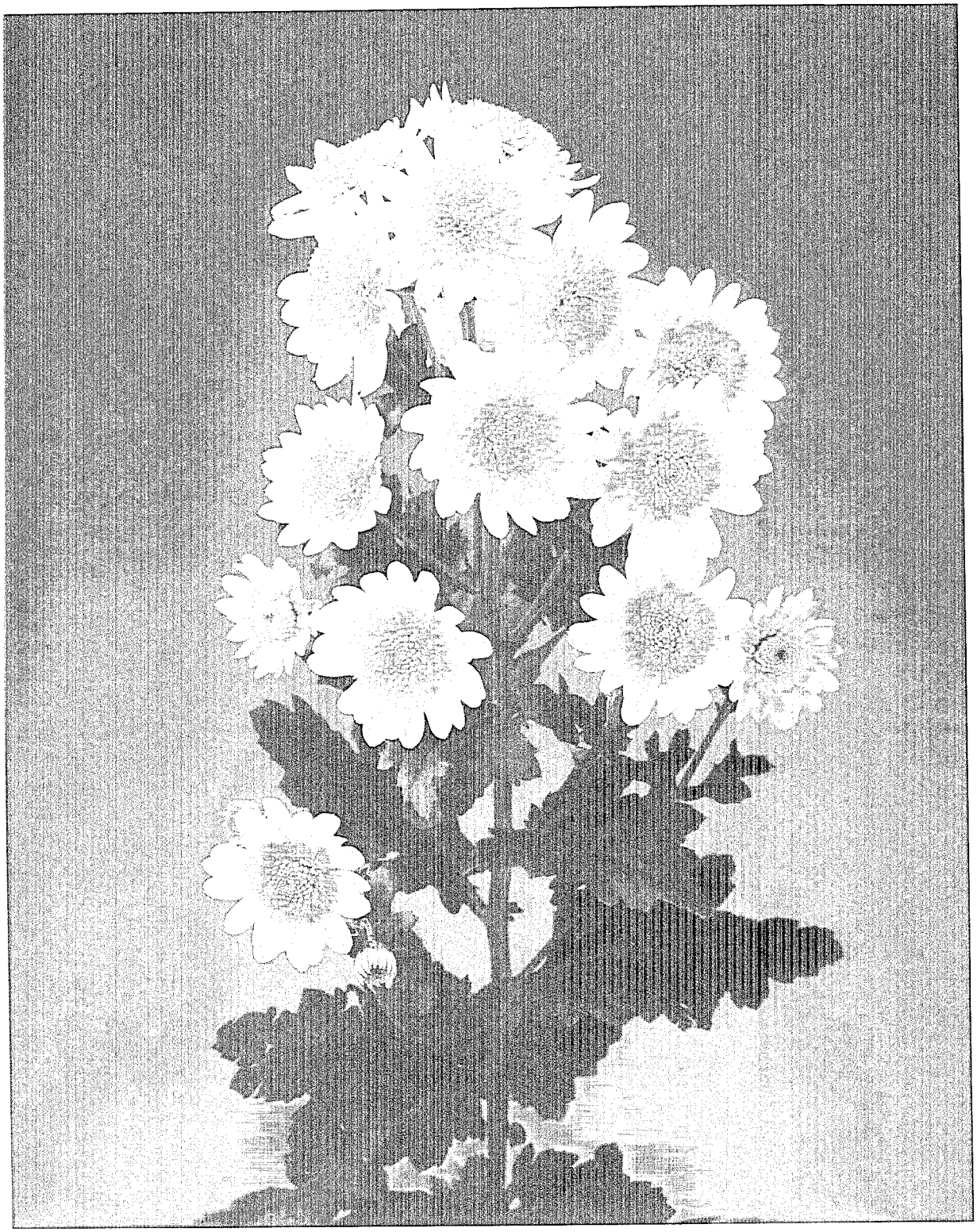

* * * * *